United States Patent [19]
Bardsley et al.

[11] Patent Number: 5,342,787
[45] Date of Patent: Aug. 30, 1994

[54] METHOD FOR SOLUBILIZING SILICA

[75] Inventors: Judy H. Bardsley, Salford; William M. Hann, Gwynedd, both of Pa.

[73] Assignee: Rohm and Haas Company, Philadelphia, Pa.

[21] Appl. No.: 36,594

[22] Filed: Mar. 24, 1993

[51] Int. Cl.$^5$ .............................. G01N 37/00
[52] U.S. Cl. ....................... 436/179; 436/72
[58] Field of Search ................ 210/698–700; 252/180, 181; 436/72, 179, 180, 182

[56] References Cited

U.S. PATENT DOCUMENTS

| | | | |
|---|---|---|---|
| 3,015,544 | 1/1962 | Shaffer, Jr. et al. | 436/72 |
| 3,193,355 | 7/1965 | Fuhrmann | 436/72 |
| 5,213,982 | 5/1993 | Soleta et al. | 436/179 |

FOREIGN PATENT DOCUMENTS

| | | | |
|---|---|---|---|
| 15754 | 1/1991 | Japan | 436/72 |
| 5568 | 1/1992 | Japan | 436/179 |
| 1190257 | 11/1985 | U.S.S.R. | 436/72 |
| 1575111 | 6/1990 | U.S.S.R. | 436/72 |
| 793792 | 4/1958 | United Kingdom | 436/72 |

OTHER PUBLICATIONS

P. M. Baker and B. R. Farrant, "Determination of Total Silicon Content of Water", Analyst, Nov., 1968, vol. 93, pp. 732–736.
Allen et al., Stability of Colloidal Silica, J. Colloid Interface Sci. 33 (1970) pp. 420–429, Published in Orlando, Fla.
Allen, et al., Stability of Colloidal Silica In The Presence Of Quarternary Ammonium Salts, J. Colloid Interface Sci., 36 (1971) pp. 289–291, Published In Orlando, Fla.
Allen, et al., Stability Of Colloidal Silica, J. Colloid Interface Sci., 31 (1969) pp. 287–296., Published in Orlanddo, Fla.
Uler, Coagulatin Of Colloidal Silica By Calcium Ions, Mechanism, And Effect Of Particle Size, J. Colloid Interface Sci., 53 (1975) pp. 476–488, Published In Orlando, Fla.
Depasse, et al., The Stability Of Amorphous Colloidal Silica, J. Colloid Interface Sci., 33 (1970) pp. 430–438, Published In Orlando, Fla.
Zerrouk, et al., Study of CA2-Induced Silica Coagulation By Small Angle Scattering, J. Colloid Interface Sci., 139 (1990) pp. 20–29, Published In Orlando, Fla.
Chemerys, Comparison Of Analytical Methods For The Determination Of Silica In Geothermal Waters. J. Vulcanology And Geothermal Research, 16 (1983) pp. 57–63.
Cheng. e tal., The Colloid Stabilities Of SiO2 Sols: The Influence of CA2+, Mg2+, EDTA And Humic Acid, Aostra Journal of Research, 7 (1991) pp. 195–200.
Fukui, et al., Study On the Determinatin Of Colloidal Silica In Boiler Feed Water, Technical Review, Sep. 1969, pp. 12–18.
Takenaka, Automated System For The Determinatin Of Total Silica In Geothermal Water By Flow Injection/Spectrophotometric Method, Bunseki Kagaku, 40 (1991) pp. 425–428 Published In Japan.
Silica DR/3000 Procedure Code S, 2, HACH DR/3000 Procedure Manual, Maughan, On–Line Silica Analysis.

Primary Examiner—Neil McCarthy
Attorney, Agent, or Firm—David T. Banchik

[57] ABSTRACT

A method for solubilizing colloidal silica in aqueous systems containing silica is provided wherein a silica-containing sample is diluted, one or more chelants are added and the pH is above 10.0.

9 Claims, No Drawings

METHOD FOR SOLUBILIZING SILICA

This present invention relates to a method for solubilizing silica. More particularly the present invention is directed to the method for solubilizing colloidal silica in aqueous systems containing silica.

Silica is one of the major fouling problems in many processes using water and it can assume many low solubility chemical forms depending on the conditions. Below about pH 7 for example, monomeric silica tends to polymerize to form oligomeric or colloidal silica. At higher pH's particularly above about pH 9.5, silica can form monomeric silicate ion. Since conversion can be slow, all of these forms may exist at any one time depending on the history of the system. Furthermore, the silicate ion can react with polyvalent cations like magnesium and calcium commonly present in process waters to produce salts with very limited solubility. Thus it is common for a mixture of many forms to be present: monomeric, oligomeric and colloidal silica; magnesium silicate, calcium silicate and other silicate salts. In describing this complex system, it is common practice to refer to the mixture merely as silica or as silica and silicate. Herein these terms are used interchangeably.

In order to prevent the problems associated with the formation of silica scale, industrial engineers generally employ one of three general approaches: limit the amount of silica present in the system, use scale prevention agents, or a combination thereof. Limiting the level of silica introduced or allowed to accumulate in the aqueous system is still the primary method of dealing with the problem.

When utilizing any of these three approaches, it is desirable to accurately know the level of silica present in the system. When relying on limiting the level of silica present in the system, if the system is flushed or replenished with make-up water when the silica levels are still low, energy and time are wasted. If the system is flushed or replenished with make-up water after the silica levels have risen too high, scale may already have formed. Similarly, it is desirable to know the level of silica so that scale prevention agents can be used economically.

It would de desirable to be able to accurately measure the level of silica in an aqueous systems such as, for example: cooling water, boiler water, geothermal processing (used to generate electricity or for heating), and sugar (particularly cane and beet) processing. In each of these processes, heat is transferred to or from the water. In three of these systems, cooling water, boiler water and sugar processing, heat is added to the water and evaporation of some of the water takes place. As the water is evaporated the silica (or silicates) will concentrate. If the silica concentration exceeds its solubility, it can deposit to form either a vitreous coating or an adherent scale that can normally be removed only by laborious mechanical or chemical cleaning. In geothermal processes, hot water laden with silica or silicates is used to heat homes or factories or is converted to steam to drive a turbine and generate electricity. At some point in each of the above four processes, heat is extracted from the water, making any dissolved silicate less soluble and thus likely to deposit on surfaces.

The current practice in these processes is to mechanically limit the amount of silica or silicates that build up in the water so that the catastrophic consequences of deposition of these compounds does not occur. For example, in cooling water, the accepted practice is to limit the amount of silica or silicates to about 180 ppm, expressed as $SiO_2$. In addition, deposition of $CaCO_3$ (which can act as a nucleating agent for silica or silicates to deposit upon) is controlled by well known inhibitors such as phosphonates or polymers such as polyacrylic acid or polymaleic acid. Because the silica is limited to 180 ppm and because in many arid areas of the US and other parts of the world make-up water may contain from 50–100 ppm silica, cooling water can only be concentrated 2 to 3 times before the risk of silica or silicate deposition becomes too great.

Similarly in boiler water, the American Society of Mechanical Engineers recommends that silica be limited to certain levels depending on the operating pressure of the boiler. For example, in low pressure boilers (less than 300 psig) the amount of silica, as $SiO_2$, should be kept below 150 ppm. As the pressure is raised, the level of silica that can be tolerated in the recirculating boiler water becomes progressively less. A polymer that would enable boilers to operate at higher cycles of concentration, particularly low pressure boilers where silica volatilization is not a great concern, would allow more energy-efficient use of the heated water.

Thus it is desirable to be able to determine the level of silica in these systems to make efficient use of the method of control, whether by limiting the amount of silica present or by adding scale control agents, and to minimize the risk of exceeding the recommended limits of silica levels.

Chemerys, "Comparison of Analytical Methods for the Determination of Silica in Geothermal Water," *Journal of Volcanology and Geothermal Research*, Vol. 16, (1983) pages 57–63 discloses for acurate colorimetric results, geothermal samples containing silica must be diluted in the field to ensure that no further polymerization occurs and that amorphous silica that may be present will redissolve. Chemerys further states that if the samples are not diluted in the field, they should be diluted in the laboratory and left standing for at least a month to allow the silica to redissolve; if analyzed immediately, the diluted samples should be made alkaline and heated overnight in a 90° C. oven. Chemerys also states that shaking seems to give better precision and accuracy, and that if the samples are not properly diluted, heating them with alkaline treatment prior to analysis gives more accurate results.

Analytical methods for determining the level of silica in a sample include colorimetric methods, spectrophotometric methods, inverse phase chromatographic methods and atomic absorption methods. These methods suffer one or more drawbacks since they are inaccurate by not taking into account the silica in its several forms, they are time-consuming, expensive, or not capable of widespread use in the field. A known method for fully solubilizing any colloidal silica present in a sample is by treating the sample with fluoride ions, such as with hydrofluoric acid; however this is an extremely hazardous and time-consuming method.

The present invention seeks to overcome these problems associated with the prior art.

According to the present invention there is provided a method of solubilizing silica in an aqueous system comprising:

diluting an aqueous silica-containing sample to provide an expected detectable silica level; and adding one or more chelants; wherein the pH of the sample is above 10.0.

The levels of silica in a sample can then be determined by any of several analytical techniques including for example, colorimetric methods, spectrophotometric methods, inverse phase chromatographic methods, atomic absorption methods, direct current plasma methods, inductively coupled plasma methods and gravimetric methods. For each technique, there is an associated range of silica levels for which the technique can provide reliable, quantitative measurements. As used herein, "detectable silica level" refers to such a range; in other words, the range of silica levels for which the analytical technique can provide reliable, quantitative measurements of the level of silica. For example, the Hach Silicomolybdate Method, a spectrophotometric technique, can reliably measure soluble silica levels up to about 30 parts per million (ppm).

Often, the level of silica in a sample is unknown. However, those skilled in the art of water treatment can approximate the level of silica in a system based on factors such as the geographical location of the water supply, the number of times the water has been recycled and other factors. As used herein, "expected" detectable silica level refers to the silica level in the diluted sample which, based on an approximation of the original silica level, will be a detectable silica level.

In addition to diluting the silica-containing sample to an expected detectable silica level, the method of the present invention utilizes one or more chelants. Chelants, well known to those skilled in the art of water-treatment, are materials which bind metal ions in solution. Suitable chelants include any material with a sufficiently high stability constant, or binding affinity, to prevent cations, for example, magnesium or iron cations from forming as their hydroxide, oxide or other anion salts at the elevated pH of the system. Examples of suitable chelants include ethylenediamine tetraacetic acid, nitrilotriacetic acid, N-(hydroxyethyl)-ethylenediamine triacetic acid, aminotris(methylenephosphonic acid), 1-hydroxyethylidene-1,1-diphosphonic acid, phosphonobutane-1,2,4-tricarboxylic acid, diethyene triamine pentamethylene phosphonate, diethylenetriamine pentaacetic acid, triethanolamine, ethylenediamine tetra(methylenephosphonic acid), hexamethylenediamine tetra(methylene phosphonic acid), and the partial and complete alkali metal and ammonium salts thereof. Preferred chelants are, for example, ethylenediamine tetraacetic acid, nitrilotriacetic acid, N-(hydroxyethyl)-ethylenediamine triacetic acid and the partial and complete sodium salts thereof. The one or more more chelants are preferably added to the silica-containing sample at a level of from about 10 to about 50,000 ppm, and most preferably from about 100 to about 5,000 ppm. The preferred level of chelant in any given sample may depend upon the level of chelatable metal species present in the sample; as the level of chelatable metal species increases, the preferred level of chelant increase.

The method of the present invention requires that the pH of the sample be above 10.0. This can be accomplished, for example, by the addition of any water-soluble organic or inorganic base. When a base is added to the sample to adjust the pH, it is preferred that the base is an alkali metal or ammonium salt, such as sodium hydroxide, potassium hydroxide or ammonium hydroxide. Most preferably, when a base is added to the sample to adjust the pH, it is sodium hydroxide. The pH of the sample may be above 10.0 as a result of the addition of the chelant. For example, the addition of the chelating agents such as tetrasodium salt of ethylenediamine tetraacetic acid or the tetrasodium salt of hydroxyethylenediamine tetraacetic acid will generally raise the pH of the sample. If the pH of the sample is above 10.0, the addition of a water-soluble organic or inorganic base is optional.

In one embodiment of the present invention, the silica-containing sample at a pH above 10 is heated after adding the one or more chelants. The sample can be heated by any conventional means such as for example, placing the container with the silica-containing sample in an oven, water-bath, or oil oil-bath. It is desirable to ensure that any loss of water due to evaporation is minimized to prevent the silica from becoming concentrated, thus resulting in an artificially high silica level measurement. The silica-containing sample is preferably heated to a temperature of from about 30° C. to about 100° C., and most preferably from about 40° C. to about 70° C.

In another embodiment of the present invention, the silica-containing sample at a pH above 10 is agitated after adding the one or more chelants. The sample can be agitated by any conventional means such as for example, placing the container with the silica-containing sample on a shaker or roller.

Preferably, the silica-containing sample at a pH above 10 is agitated and heated after adding the one or more chelants.

Preferably, the silica-containing sample at a pH above 10 is maintained in the presence of the one or more chelants for a period of time before the level of silica is measured. Preferably, the silica-containing sample at a pH above 10 is maintained in the presence of the one or more chelants for a period of from about 30 minutes to about 36 hours, and most preferably from about 45 minutes to about 24 hours before the level of silica is measured.

As a result of the present invention, silica is solubilized reasonably quickly, easily and inexpensively. Thus, quantitative determinations of the level of silica in a silica-containing sample can be made accurately and quickly by any available analytical method including colorimetric methods, spectrophotometric methods, inverse phase chromatographic methods and atomic absorption methods. Preferably, the analytical method is a colorimetric or spectrophotometric method.

The following test was employed to demonstrate the method of the present invention for solubilizing silica. The test procedure used was one which simulated silica-laden process water conditions.

An aqueous silica stock solution was prepared in the following manner:
  3.48 grams N ® Clear Sodium Silicate (a trademark of the PQ Corporation) (28.7 percent by weight aqueous $SiO_2$) was diluted to 1 liter with deionized water.

An aqueous sodium bicarbonate stock solution was prepared in the following manner:
  5.60 grains of $NaHCO_3$ was diluted to 1 liter with deionized water, An aqueous calcium/magnesium stock solution was prepared in the following manner:
  1.83 grams $CaCl_2.2H_2O$ and 1.52 grams of $MgCl_2.6H_2O$ were diluted to 1 liter with deionized water.

Simulated cooling water was prepared in the following manner:
  To a 4 ounce plastic jar was added:

40 grams of the silica stock solution
15 grams of the sodium bicarbonate stock solution
40 grams of the calcium/magnesium stock solution
5 grams of deionized water The simulated cooling water was allowed to stand at room temperature for 11 days.

The levels of the various components of the simulated cooling water was as follows:

400 ppm Si as $SiO_2$
300 ppm $Mg^{+2}$ (as $CaCO_3$)
500 ppm $Ca^{+2}$ (as $CaCO_3$)

After standing at room temperature for 11 days, a 30 gram sample of the simulated cooling water was taken and diluted to 1,000 grams with deionized water.

EXAMPLE 1

The silica level of the diluted simulated cooling water was measured by the Hach Silicomolybdate Method which involves the reaction of molybdate ion with silica and phosphate to form a yellow color. Citric acid is added to destroy the phosphomolybdic acid complex but not the silicomolybdic acid complex. The level of silicomolybdate acid complex is determined by spectrophotometric techniques (total absorbance at 410.0 nm). The data for Example 1 appearing in Table I, below, is the measured value (Hach method) of the level of silica taking into account the dilution of the sample. The measurement was repeated after 1 hour, 4 hours and 24 hours.

Example 2 was conducted in a similar manner as Example 1 except that to a 100 gram sample of the diluted simulated cooling water was added 0.4 grams of a 1 percent by weight aqueous sodium hydroxide solution.

Example 3 was conducted in a similar manner as Example 1 except that to a 100 gram sample of the diluted simulated cooling water was added 1.0 gram of a 40 percent by weight aqueous solution of ethylenediaminetetraacetic acid, tetrasodium salt.

Example 4 was conducted in a similar manner as Example 1 except that to a 100 gram sample of the diluted simulated cooling water were added 0.4 grams of a 1 percent by weight aqueous sodium hydroxide solution and 1.0 gram of a 40 percent by weight aqueous solution of ethylenediaminetetraacetic acid, tetrasodium salt.

Example 5 was conducted in a similar manner as Example 1 except that to a 100 gram sample of the diluted simulated cooling water were added 0.2 grams of a 1 percent by weight aqueous sodium hydroxide solution and 0.5 grams of a 40 percent by weight aqueous solution of ethylenediaminetetraacetic acid, tetrasodium salt.

Example 6 was conducted in a similar manner as Example 4 except that the sample was placed on a mechanical shaker and was continuously shaken.

Example 7 was conducted in a similar manner as Example 4 except that the sample was maintained at 50° C.

Example 8 was conducted in a similar manner as Example 4 except that the sample was placed on a mechanical roller and was continuously rolled while maintaining the sample at 50° C.

TABLE I

MEASURED SILICA LEVELS IN SAMPLES CONTAINING 400 ppm SILICA

| Example | Conditions | Measured $SiO_2$ Level (ppm) | | | | pH |
|---|---|---|---|---|---|---|
| | | Initial | 1 hr | 4 hrs | 24 hrs | |
| 1 | Dilution only | 137 | 143 | 173 | 370 | 9.3 |
| 2 | Dilution and 0.004% NaOH | | 150 | 167 | 403 | 11.0 |
| 3 | Dilution, 0.4% $Na_4EDTA$ | | 216 | 360 | 403 | 10.9 |
| 4 | Dilution, 0.4% $Na_4EDTA$ and 0.004% NaOH | | 186 | 367 | 400 | 11.2 |
| 5 | Dilution, 0.2% $Na_4EDTA$ and 0.002% NaOH | | 206 | 400 | 410 | 11.0 |
| 6 | Dilution, 0.4% $Na_4EDTA$, 0.004% NaOH and shaking | | 196 | 393 | 397 | 11.2 |
| 7 | Dilution, 0.4% $Na_4EDTA$, 0.004% NaOH, 50° C. | | 383 | 443* | 423* | 11.2 |
| 8 | Dilution, 0.4% $Na_4EDTA$, 0.004% NaOH, rolling, 50° C. | | 406 | 417 | 470* | 11.2 |

*Samples may have been improperly sealed, resulting in evaporation of some of the water.

As can be seen by the data in Table 1, above, the silica in the silica-containing samples at pH 10.0 or above are substantially solubilized in the presence of a chelant in a reasonable period of time.

We claim:

1. A method of solubilizing silica in an aqueous system comprising:
   diluting an aqueous silica-containing sample to provide an expected detectable silica level; and
   adding one or more chelants; wherein the pH of the sample is above 10.0.

2. The method of claim 1, wherein: the one or more chelants are selected from the group consisting of ethylenediamine tetraacetic acid, nitrilotriacetic acid, N-(hydroxyethyl)-ethylenediamine triacetic acid, aminotris(methylenephosphonic acid), 1-hydroxyethylidene-1,1-diphosphonic acid, 2-phosphonobutane-1,2,4-tricarboxylic acid, diethyene triamine pentamethylene phosphonate, diethylenetriamine pentaacetic acid, triethanolamine, ethylenediamine tetra(methylenephosphonic acid), hexamethylenediamine tetra(methylene phosphonic acid), and the partial and complete alkali metal and ammonium salts thereof.

3. The method of claim 1, wherein: the one or more chelants are selected from the group consisting of ethylenediamine tetraacetic acid, nitrilotriacetic acid, N-(hydroxyethyl)-ethylenediamine triacetic acid and the partial and complete sodium salts thereof.

4. The method of claim 1, wherein: the chelant is ethylenediamine tetraacetic acid or the partial or complete sodium salt thereof.

5. The method of claim 1, further comprising: heating the silica-containing sample to a temperature of from about 30° C. to about 100° C.

6. The method of claim 1, further comprising: heating the silica-containing sample to a temperature of from about 40° C. to about 70° C.

7. The method of claim 1, further comprising: agitating the silica-containing sample.

8. The method of claim 1, further comprising: agitating and heating the silica-containing sample to a temperature of from about 30° C. to about 100° C.

9. A method of solubilizing silica in an aqueous system comprising:
   diluting an aqueous silica-containing sample to provide a silica level of below about 30 ppm; and
   adding one or more chelants; wherein the pH of the sample is above 10.0.

* * * * *